United States Patent
Sarkar et al.

(10) Patent No.: US 11,628,274 B2
(45) Date of Patent: *Apr. 18, 2023

(54) DEVICE AND METHOD FOR AUTOMATED EMERGENCY ARTERIAL SHEATH PLACEMENT

(71) Applicant: UNIVERSITY OF MARYLAND, BALTIMORE, Baltimore, MD (US)

(72) Inventors: Rajabrata Sarkar, Ellicott City, MD (US); Robert Crawford, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 2 days.

This patent is subject to a terminal disclaimer.

(21) Appl. No.: 16/891,636

(22) Filed: Jun. 3, 2020

(65) Prior Publication Data
US 2020/0360661 A1 Nov. 19, 2020

Related U.S. Application Data

(63) Continuation of application No. 15/742,060, filed as application No. PCT/US2016/041291 on Jul. 7, 2016, now Pat. No. 10,702,676.
(Continued)

(51) Int. Cl.
*A61M 25/01* (2006.01)
*A61M 5/42* (2006.01)
(Continued)

(52) U.S. Cl.
CPC ........ *A61M 25/0113* (2013.01); *A61M 5/427* (2013.01); *A61M 25/065* (2013.01);
(Continued)

(58) Field of Classification Search
CPC .... A61M 5/42; A61M 5/427; A61M 25/0606; A61M 25/065
See application file for complete search history.

(56) References Cited

U.S. PATENT DOCUMENTS

6,379,307 B1 4/2002 Filly et al.
10,702,676 B2 * 7/2020 Sarkar ................... A61M 5/427
(Continued)

*Primary Examiner* — Todd J Scherbel
(74) *Attorney, Agent, or Firm* — Whiteford, Taylor & Preston, LLP; Gregory M. Stone (57) ABSTRACT

Disclosed are devices and methods for automated emergency arterial cannulation. The device comprises a hand-held automated emergency arterial sheath placement device having a body with a handle and an actuator, and an arterial sheath placement head at the distal end of the handle body configured for placement against the patient's skin. The arterial sheath placement head includes an arterial sheath insertion device configured to advance an arterial needle, guide wire, and arterial sheath into a patient's artery upon sequential operation of the actuator. The arterial sheath placement head also includes a non-invasive artery locator configured to locate an artery into which the arterial sheath is intended to be placed. The arterial sheath placement head also preferably includes a Doppler gel and antiseptic needle, a local anesthetic needle, and a scalpel, all of which are likewise configured to advance from the upper body portion upon sequential operation of the actuator.

12 Claims, 7 Drawing Sheets

Related U.S. Application Data (60) Provisional application No. 62/189,296, filed on Jul. 7, 2015.

(51) Int. Cl.
*A61M 25/06* (2006.01)
*A61M 25/09* (2006.01)
*A61M 25/00* (2006.01)

(52) U.S. Cl.
CPC . *A61M 25/0606* (2013.01); *A61B 2562/0247* (2013.01); *A61M 25/09041* (2013.01); *A61M 2025/0002* (2013.01); *A61M 2205/3317* (2013.01); *A61M 2205/3344* (2013.01)

(56) References Cited

U.S. PATENT DOCUMENTS

| | | | |
|---|---|---|---|
| 2002/0133079 A1 | 9/2002 | Sandhu | |
| 2003/0060716 A1* | 3/2003 | Heidrich | A61M 25/0612 600/464 |
| 2007/0073155 A1 | 3/2007 | Park et al. | |
| 2013/0178711 A1* | 7/2013 | Avneri | A61B 17/3403 604/164.13 |

\* cited by examiner

DEVICE AND METHOD FOR AUTOMATED EMERGENCY ARTERIAL SHEATH PLACEMENT

CROSS REFERENCE TO RELATED APPLICATIONS

This application is a continuation of U.S. patent application Ser. No. 15/742,060, titled "DEVICE AND METHOD FOR AUTOMATED EMERGENCY ARTERIAL SHEATH PLACEMENT" and filed on Jan. 5, 2018, which is a national stage entry of PCT/US16/41291, titled "DEVICE AND METHOD FOR AUTOMATED EMERGENCY ARTERIAL SHEATH PLACEMENT" and filed on Jul. 7, 2016, which is based upon and claims priority from U.S. Provisional Patent Application No. 62/189,296, titled "Automated Emergency Femoral Artery Sheath Placement Device" and filed on Jul. 7, 2015 by the inventors herein, which is hereby incorporated by reference for all purposes as if fully set forth herein.

FIELD OF THE INVENTION

The present invention relates generally to the fields of cardiovascular and emergency medicine. More specifically, the present invention relates to automated arterial sheath placement (such as for use with the Resuscitative Endovascular Balloon Occlusion of the Aorta (REBOA) technique), and more particularly to an automated emergency femoral artery sheath placement device.

BACKGROUND

Arterial cannulation is used widely in the clinical management of critically ill adults, with intra-arterial cannula placement second in frequency only to intravenous cannulation. It provides an uninterrupted display of pulse contour and continuous beat-to-beat haemodynamic measurement. This data can be invaluable for effective clinical management, such as the reliable titration of supportive medications. Numerous patient conditions, including morbid obesity, burns or trauma to the extremities and shock can cause non-invasive blood pressure measurements to be inaccurate, and thus necessitate invasive blood pressure monitoring. The procedure of arterial cannulation comes with some risk, such that the need must be weighed against the risk to the patient. Arterial cannulation may be performed on a number of vessels including the radial, femoral, axillary, brachial, ulnar, dorsal pedis, tibial posterior and temporal arteries. Arterial cannulation is also essential for gaining access to the arterial system for angiography and placement of guidewires, balloon pumps, catheters and stents.

This disclosure focuses on arterial cannulation, and in particular embodiments on femoral artery cannulation, which has numerous advantages over cannulation of other sites. Femoral cannulation provides a pulse contour approximating aortic with minimal thrombotic risk. There is little evidence to show increased incidence of catheter-related systemic infection at this site.

Figure 1:
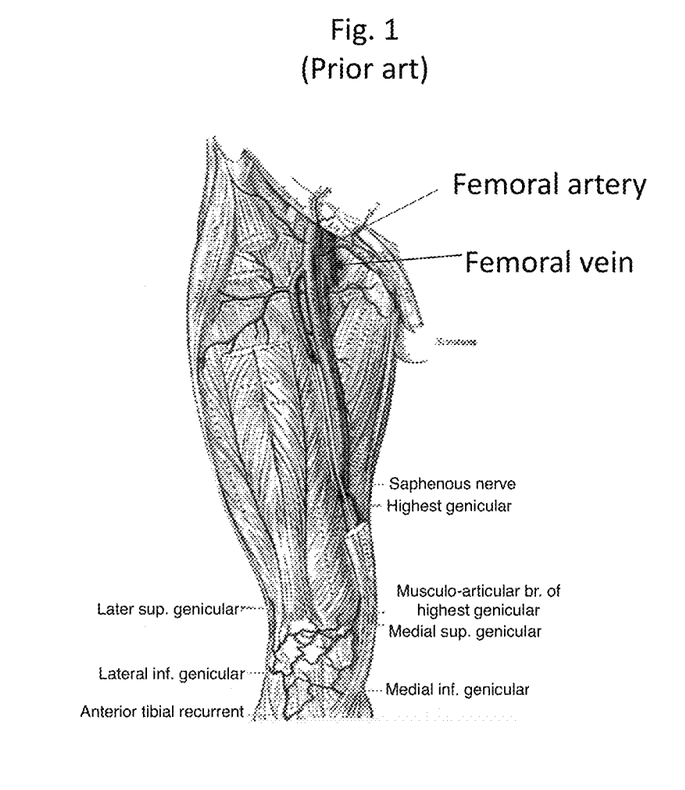
FIG. 1 shows a schematic view of a femoral artery lying in a neurovascular bundle lateral to the femoral vein and median to the femoral nerve.

The femoral artery lies in a neurovascular bundle lateral to the femoral vein and median to the femoral nerve (as seen in FIG. 1). The femoral artery is palpated midway between the anterosuperior iliac spine and the symphysis pubis. Collateral circulation exists via a number of anastomoses, and the large vessel diameter allows catheter longevity twice that of radial catheters. Prospective and retrospective studies detail the relative safety of this site for hemodynamic monitoring. A potential exists, however, for extraperitoneal hemorrhage, vascular injury from common branch entry, and cannulation hematoma. Femoral artery catheter complications, though infrequent, are complicated, difficult to identify, and may be associated with significant mortality. The femoral artery usually can be cannulated, even during profound shock states.

An important application for the procedure is emergent or urgent cannulation of the femoral artery for subsequent placement of a REBOA balloon or intraaortic balloon pump. REBOA is Resuscitative Endovascular Balloon Occlusion of the Aorta and is a lifesaving device for use in patients with pelvic fractures, penetrating injuries, life threatening hemorrhage, ruptured abdominal aortic aneurysms, and other emergency conditions. REBOA may have the greatest benefit when deployed early, and has been applied in the field (pre-ambulance) in Europe. There is clear military importance in deployment of REBOA in the field. An intra-aortic balloon pump is used to support patients in cardiogenic shock, and is also often deployed under urgent or emergent conditions.

Femoral artery cannulation is a valuable procedure, but at present clinicians with advanced training must perform the procedure. Cannulation and sheath placement in the femoral artery currently requires a physician with advanced training (e.g., training in vascular surgery, trauma surgery, interventional radiology or interventional cardiology) and involves multiple needle, scalpel and wire exchanges (Seldinger technique, see FIG. 2). In an emergency setting, the femoral pulse may be absent or decreased due to hypotension which further complicates accurate localization for cannulation. The absence or limited availability of properly trained clinicians in all emergency or military settings limits the current applicability of REBOA or other invasive resuscitative or monitoring techniques. Earlier pre-hospital use of these techniques would increase survival, but requires accurate femoral artery cannulation in settings where the available personnel lack the training for conventional femoral artery cannulation.

Therefore, there remains a need in the art for systems and methods that will enable arterial cannulation, and more particularly femoral artery cannulation, in an emergency setting by persons lacking the traditional advanced training in arterial cannulation, and that allow such arterial cannulation to be carried out quickly, easily, effectively, and safely by such persons.

The above information disclosed in this Background section is only for enhancement of understanding of the background of the invention and therefore it may contain information that does not form any part of the prior art.

SUMMARY OF THE INVENTION

Disclosed herein are devices and methods for arterial cannulation that allow such process to be carried out in an emergency setting by persons lacking the traditional advanced training in arterial cannulation, and that allow such arterial cannulation to be carried out quickly, easily, effectively, and safely by such persons. The device comprises a hand-held automated emergency arterial sheath placement device having a body with a handle and a trigger or similarly configured actuator, and an arterial sheath placement head at the distal end of the handle body configured for placement against the patient's skin. The arterial sheath placement head includes an upper body portion that is separable from a lower body portion, with the upper body portion preferably configured as a disposable unit. Such detachable upper body portion includes at least an arterial sheath insertion device configured to advance an arterial needle, guide wire, and arterial sheath into a patient's artery upon sequential operation of the actuator. The lower body portion of the arterial sheath placement head includes a non-invasive artery locator, such as a Doppler sensor configured to locate an artery into which the arterial sheath is intended to be placed. The upper body portion also preferably includes a Doppler gel and antiseptic needle, a local anesthetic needle, and a scalpel, all of which are likewise configured to advance from the upper body portion upon sequential operation of the actuator. With such a configuration, arterial sheath placement can be achieved by simple proper placement of the device on the patient's body (which proper placement is determined by the non-invasive artery locator), followed by sequential operation of the actuator to advance the various elements within the upper body, thus greatly simplifying the arterial sheath placement process and allowing such process to be carried out quickly and safely in emergency conditions, even by persons lacking the traditional experience that has previously been required for proper arterial sheath placement.

One of the purposes of this invention is to provide a device that may enable a larger group of clinicians with less training to effectively and safely perform the procedure, including "in the field" (e.g., femoral artery sheath placement procedures performed by emergency personnel in an ambulance at the scene of an accident). However, achieving the above purposes and/or benefits is not a necessary feature of each of the exemplary embodiments, and claims may recite subject matter that does not achieve the above stated purpose.

In accordance with certain aspects of an embodiment of the invention, an automated emergency arterial sheath placement device is provided, comprising: a body including a handle; an arterial sheath placement head attached to the body, the arterial sheath placement head comprising a non-invasive artery locator and an arterial sheath insertion device; and a manually operable actuator; wherein the arterial sheath insertion device is positioned with respect to the artery locator so as to position the arterial sheath insertion device over an artery that has been located by the artery locator, and wherein the automated emergency arterial sheath placement device is configured to cause the arterial sheath insertion device to install an arterial sheath in a patient's artery upon sequential activation of the actuator.

In accordance with further aspects of an embodiment of the invention, a method is provided for performing automated emergency arterial sheath placement, comprising the steps of: providing an automated emergency arterial sheath placement device, comprising a body including a handle; an arterial sheath placement head attached to the body, the arterial sheath placement head comprising a non-invasive artery locator and an arterial sheath insertion device; and a manually operable actuator; wherein the arterial sheath insertion device is positioned with respect to the artery locator so as to position the arterial sheath insertion device over an artery that has been located by the artery locator, and wherein the automated emergency arterial sheath placement device is configured to cause the arterial sheath insertion device to install an arterial sheath in a patient's artery upon sequential activation of the actuator; positioning the automated emergency arterial sheath placement device over a patient's femoral region; moving the automated emergency arterial sheath placement device across the patient's groin until the artery locator detects that the arterial sheath insertion device is positioned over a femoral artery of the patient; sequentially engaging the actuator to cause the arterial sheath insertion device to insert an arterial sheath into the femoral artery of the patient; and preferably confirming actual intra-arterial sheath placement by automatic determination of appropriate femoral artery waveforms within the sheath.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

FIG. 3 (a) shows schematically a side view of an arterial sheath placement device according to an exemplary embodiment of the invention.

FIG. 3 (b) shows schematically a front view of the arterial sheath placement head of an arterial sheath placement device according to certain aspects of an exemplary embodiment of the invention.

DETAILED DESCRIPTION

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art. Descriptions of well-known functions and structures are omitted to enhance clarity and conciseness.

Hereinafter, an automated emergency femoral artery sheath placement device and method is disclosed. This invention may, however, be embodied in many different forms and should not be construed as limited to the exemplary embodiments set forth herein. Rather, these exemplary embodiments are provided so that this disclosure is thorough, and will fully convey the scope of the invention to those skilled in the art.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The disclosure herein presents a portable, hand-held, and optionally battery-powered device for arterial cannulation, and in a particular embodiment for femoral artery cannulation, that uses a Doppler sensor to identify non-palpable femoral blood flow so as to automate and improve upon the Seldinger technique (FIG. 2) to allow arterial cannulation, and more particularly femoral artery cannulation, to be accomplished by persons lacking traditional specialized training in arterial cannulation techniques. The device is referred to at times herein as an Automated Emergency Femoral Artery Sheath Placement ("eFASP") device. No such devices are known to the inventors to be available that allow emergency providers (physicians or non-physicians) without specialized training to obtain rapid femoral artery access and sheath placement in an emergency or pre-hospital setting. Additional applications of this device may include:

1) Urgent placement of a femoral artery sheath for blood pressure monitoring and blood gas sampling in the emergency room; hypotensive patients requiring pressor therapy or going to procedures involving invasive arterial line placement. This invention could rapidly facilitate these procedures in critically ill and/or hypotensive patients.

2) Accurate cannulation of the femoral artery by emergency room personnel in preparation for cardiac catheterization. Acute myocardial infarction patients require emergent cardiac catheterization where the interventional cardiologist accesses the femoral artery as the first step. This device could allow emergency room or catheterization lab personnel to pre-place the sheath and potentially decrease "door to balloon" times.

3) Variants of this device would permit safer and easier radial and brachial artery cannulation. Access to the radial artery for blood pressure monitoring and blood gas sampling is commonly done in the operating room and ICU, as is brachial artery access. Both are associated with a high rate of failure under emergency conditions in hypotensive patients as well as potentially significant complications.

The Automated Emergency Femoral Artery Sheath Placement device according to certain aspects of an embodiment of the invention is designed to allow emergency medical providers without specialized vascular training to rapidly and accurately obtain femoral artery sheath access under emergency conditions without the use of external ultrasound or other imaging equipment. The device is self-contained and does not require external wires, scalpels, imaging, etc., which are all currently required for conventional femoral sheath placement.

Figure 2:
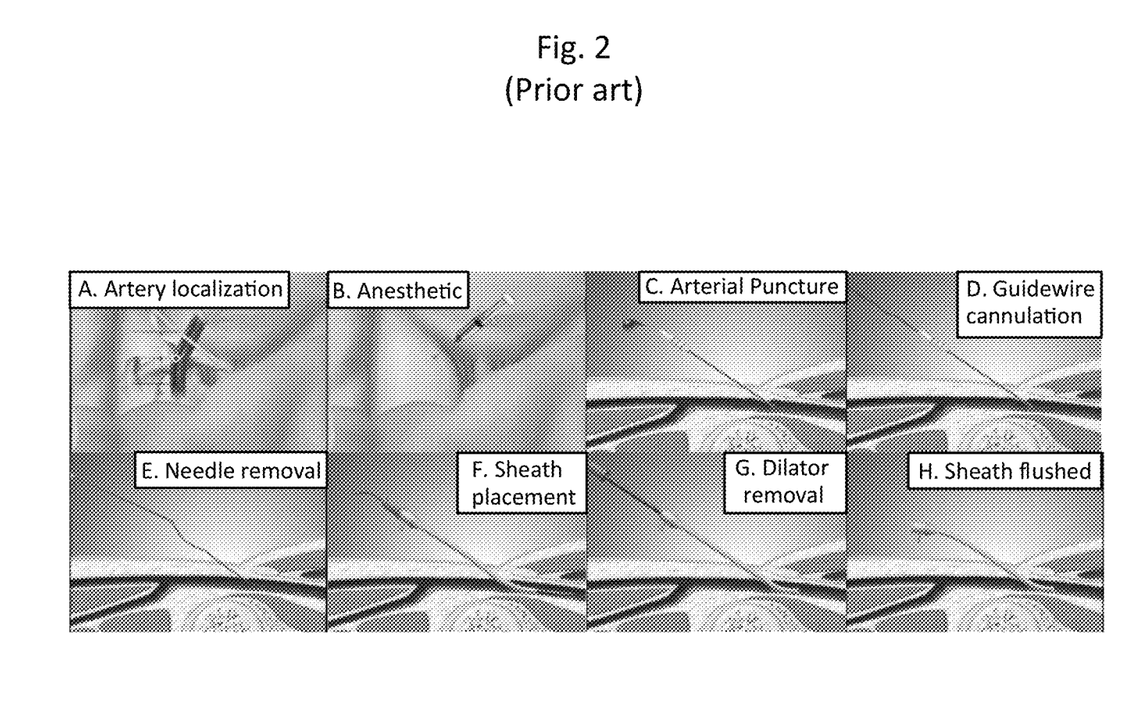
FIG. 2 shows the steps involved in performing cannulation and sheath placement in the femoral artery according to the Seldinger technique.
Figure 3A:
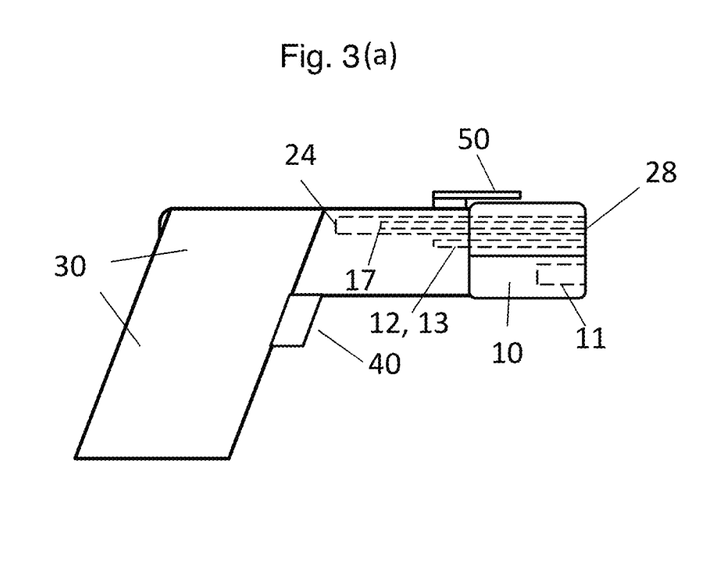

Traditional femoral artery cannulation involves multiple, distinct clinical steps and varied items of equipment, including needles, a scalpel, wire exchanges, and sheaths, all as shown in FIG. 2 (depicting the "Seldinger technique"). The device disclosed herein incorporates preferably all components required for arterial cannulation into a single compact and easy to operate device—the Automated Emergency Femoral Artery Sheath Placement device. FIG. 3(a) shows a side view of an eFASP device according to an exemplary embodiment of the invention. The eFASP device may include a handle body 30, an arterial sheath placement head (shown generally at 10) attached to a distal end of handle body 30, a manually operable actuator such as a trigger 40, an LCD display screen 50, and a battery (not shown) in communication with a motor (described further below) that engages the various elements required for arterial cannulation, all of which are discussed in greater detail below. The eFASP is configured such that an operator holds the handle body 30 and operates the trigger 40 by his/her finger in a manner similar to operating a cordless drill. When held in this manner, a skin-facing outer wall 28 of arterial sheath placement head 10 may be placed against a patient's skin for arterial cannulation. The arterial sheath placement head 10 includes a non-invasive artery locator, such as a Doppler sensor 11 (discussed in greater detail below), that is used to properly position the arterial sheath placement head 10 over a patient's artery that is to receive an arterial sheath. The arterial sheath placement head 10 also includes an arterial sheath insertion device that is positioned with respect to the non-invasive artery locator to allow automated insertion of an arterial sheath into the patient's artery when the artery locator detects that it is in proper position over such artery. Trigger 40 is preferably manually operated by an operator to sequentially operate the elements of the arterial sheath insertion device, and preferably additional elements in arterial sheath placement head 10 (e.g., a Doppler gel and antiseptic application needle, a local anesthetic needle, and a scalpel), so as to automate the process of inserting an arterial sheath into the patient's artery simply through positioning the eFASP and sequentially engaging trigger 40.

Figure 3B:
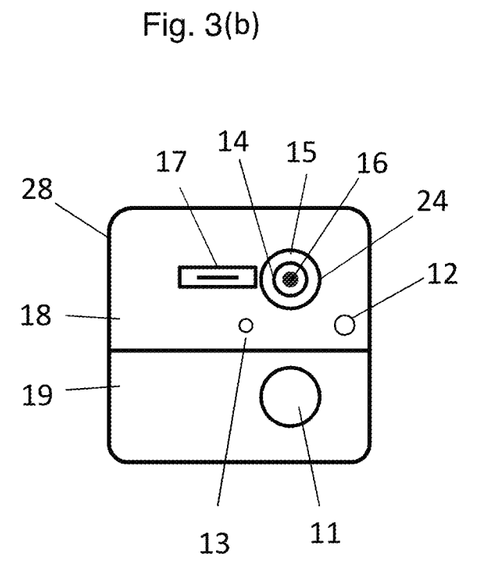

FIG. 3(b) shows a front view of arterial sheath placement head 10, and more particularly of skin-facing outer wall 28 of arterial sheath placement head 10. Arterial sheath placement head 10 includes a Doppler sensor 11, which Doppler sensor 11 is in electrical communication with associated electronic components positioned within head 10 and/or handle body 30. A wide variety of Doppler sensors 11 and their associated electronic components are readily commercially available and suitable for use with the embodiments disclosed herein, and thus are not further detailed here. By way of non-limiting example, a prototype of the eFASP has incorporated an 8 MHz True Sonotrax vascular Doppler unit. The electronics associated with the eFASP are standard commercially available units (e.g., Arduino processor), which are programmed to integrate pressure and stepper motor data and display findings to the operator.

Figure 4A:
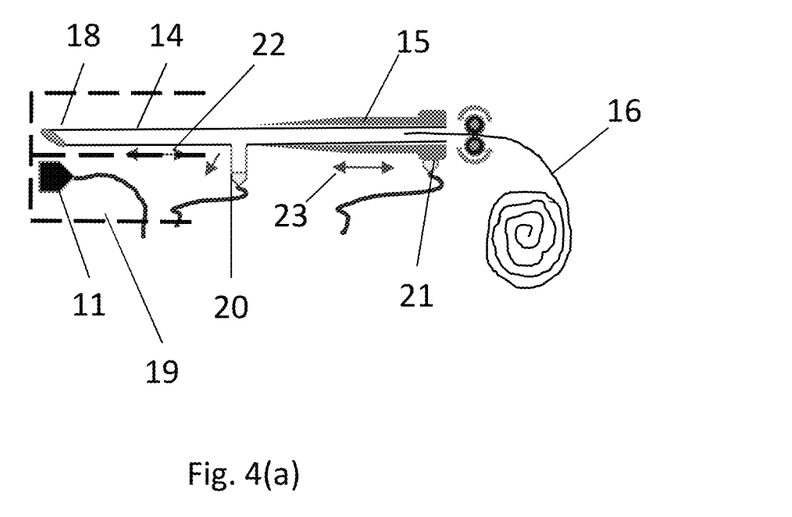
FIG. 4(a) shows a schematic side view of an arterial needle/guide wire/arterial sheath unit according to certain aspects of an exemplary embodiment of the invention.
Figure 4B:
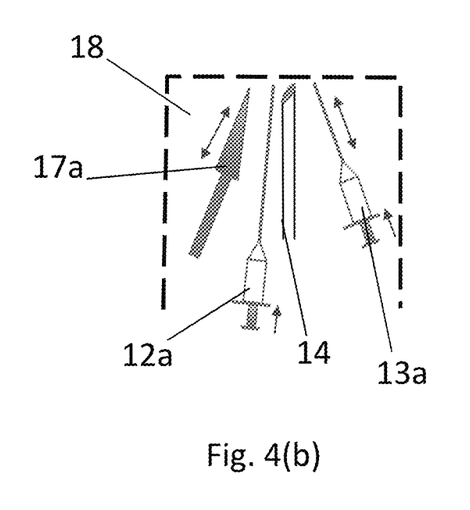
FIG. 4(b) shows a schematic top view of the scalpel, the gel/antiseptic needle and the anesthetic needle arrangement relative to the arterial entry needle according to certain aspects of an exemplary embodiment of the invention.

Arterial sheath placement head 10 also includes a Doppler gel injector/applicator port 12 through which a Doppler gel injector/applicator needle 12a (FIG. 4(b)) may extend to engage a patient's skin to apply Doppler gel and antiseptic thereto. Arterial sheath placement head 10 further includes an anesthetic injector port 13 through which an anesthetic injector 13a (FIG. 4(b)) may extend to apply anesthetic to the portion of the patient's body (e.g., their groin) that is to receive an arterial sheath. Still further, arterial sheath placement head 10 includes an arterial sheath port 24 through which an arterial entry needle 14, a sheath 15, and a guide wire 16 may extend for ultimate arterial sheath placement within a patient's artery. Finally, arterial sheath placement head 10 includes a scalpel port 17 through which a scalpel 17a (FIG. 4(b)) may extend to incise a portion of the patient's skin prior to introduction of the arterial sheath 15 into the patient's artery. As shown in FIG. 3(a), each of Doppler gel injector/applicator port 12, anesthetic injector port 13, arterial sheath port 24, and scalpel port 17, along with Doppler sensor 11, may extend from skin-facing outer wall 28 into the body of arterial sheath placement head 10, and optionally into handle body 30, with their respective moveable patient-engaging elements (i.e., Doppler gel injector/applicator 12a, anesthetic injector 13a, arterial needle 14, arterial sheath 15, guide wire 16, and scalpel 17) being moveable within their respective ports. Arterial needle 14, arterial sheath 15, and guide wire 16 may be disposed concentrically as shown by FIG. 3(b).

Arterial sheath placement head 10 may include an upper body unit 18 and a lower body control unit 19, with upper body unit 18 preferably being separable from handle body 30 and from lower body control unit 19. Upper body unit 18 may include the Doppler gel injector port 12, anesthetic injector port 13, arterial sheath port 24, and scalpel port 17, while lower body control unit 19 preferably houses Doppler sensor 11.

According to exemplary embodiments of the invention, the sizes of the components within arterial sheath placement head 10 and the distances between such components may be as follows. Arterial sheath 15 may be about 3-4 mm in diameter. Arterial needle 14 may have a diameter which is about 1 mm smaller than the diameter of arterial sheath 15. Guide wire 16 may be about 2 mm in diameter. Doppler sensor 11 may be about 10 mm in diameter.

Further, arterial needle 14 may be about 12 inches long and may have a motion range of about 3 inches. Arterial sheath 15 may be about 4 inches long. Guide wire 16 may be about 36 inches long. The range of motion for arterial sheath 15 may be about 4 inches (it will be almost completely within the patient at the end of the procedure). The range of motion for guide wire 16 may be about 9 inches forward. Scalpel 17 may be a size #11 blade or may be about 4 mm wide and about 10 mm long.

Still further, the distance between the centers of Doppler sensor 11 and arterial sheath 15 may be about 3 cm, with the center of arterial sheath 15 generally in vertical alignment with the center of Doppler sensor 11. The distance between the center of scalpel port 17 and the center of Doppler sensor 11 may be approximately 5 cm. The distance between the center of scalpel port 17 and the center of guide wire 16 may be about 4 cm, with the center of scalpel port 17 generally in horizontal alignment with the center of guide wire 16. Moreover, as shown in FIG. 4(b) and discussed in greater detail below, Doppler gel injector/applicator 12a, anesthetic injector 13a, and scalpel 17a (and their respective ports) may be situated at angles to arterial needle 14 to allow each of them to intersect a patient's body at the appropriate and intended location with respect to the artery that is to receive arterial sheath 15. Also, the sides of skin-facing outer wall 28 of arterial sheath placement head 10 may be about 6 cm long. As the average common femoral artery is about 12 mm in diameter and approximately 3-6 cm below the skin, the foregoing dimensions are suitable for average applications of the devices and methods set forth herein.

It will be understood by those skilled in the art that the above dimensions are provided as exemplary only, and that various changes in form and details may be made thereto without departing from the spirit and scope of the present disclosure as defined by the appended claims. For example, the spacing of Doppler sensor 11, needles 12 and 13, and scalpel 17 with respect to sheath 15 may be altered to provide systems particularly sized for differing body sizes or arterial targets, such as pediatric versus full-grown adults or radial versus femoral arteries, and the length and diameters of such elements may similarly be adjusted, all without departing from the spirit and scope of the invention.

As mentioned above, arterial sheath placement head 10 may be configured such that upper body 18 and lower body control unit 19 may be separable from each other. Moreover, upper body 18 may be disposable and sterilized. The upper body 18 is preferably packaged in a sterile peel-pack and incorporates all components of the eFASP that contact the patient (i.e., needles, guidewires, solutions, etc.). Upper body 18 is thus preferably configured for single-use only. The control unit 19 may include the Doppler sensor 11 and the associated electronic components, and in a typical configuration is not disposable. There are no components of the eFASP that enter the patient that are in control unit 19. The front aspect of control unit 19 touches the skin to allow the Doppler probe to localize the femoral artery. As with any reusable Doppler probe, the front of control unit 19 will be cleaned with standard cleanser between uses. The two units 18 and 19 are preferably configured to detachably lock together. By way of non-limiting example and in accordance with certain aspects of an embodiment, the units may have clips that lock together and a series of mechanical and electronic interfaces that allow the motors within control unit 19 to move the disposable components (e.g. needle, sheath, etc.) as well as detect electronic signals from the pressure transducers within the upper disposable unit 18. The locking together of units 18 and 19 may be performed in either a completely sterile (operating room) or semi-sterile (pre-hospital use) manner. The sterile configuration is achieved by having a clear sterile bag attached to disposable upper body unit 18 that is pulled down to encompass and wrap the control unit. The sterile bag is then tied securely and the operator can actuate the trigger and observe the display unit through the bag. The eFASP resembles in size and configuration a cordless drill when docked.

FIGS. 4(a) and 4(b) show exemplary embodiments of the components that may be incorporated in arterial sheath placement head 10, including needle 12a for releasing Doppler gel and antiseptic, needle 13a for injecting anesthetic, arterial needle 14, and scalpel 17a. The eFASP may further include a first pressure transducer 20 configured to measure the pressure inside the lumen of the arterial needle 14, and a second pressure transducer 21 mounted on the sheath and configured to measure the pressure inside the lumen of the arterial sheath 15 (as seen in FIG. 4(a)). The first pressure transducer 20 is configured to break away upon moving/sliding the arterial sheath 15 over the arterial needle 14.

FIG. 4(a) shows the configuration and relative positions of the Doppler sensor 11, arterial needle 14, arterial sheath 15, and guide wire 16 within the device head 10 (partially shown in phantom for clarity) and the body 30 according to an exemplary embodiment of the invention. In an exemplary embodiment, the entire assembly shown in FIG. 4(a) is contained entirely within disposable upper body unit 18. As may be seen in FIG. 4(a), advancement of arterial sheath 15 over arterial needle 14 may detach side-mounted pressure transducer 20 from a side of arterial needle 14, allowing its insertion into an artery in the patient. Movements of arterial needle 14 and of arterial sheath 15 with respect to arterial needle 14 are shown by arrows 22 and 23, respectively. A drive mechanism, such as by way of non-limiting example a rack and pinion assembly, may be provided for driving arterial needle 14 and arterial sheath 15, which mechanical drive elements are omitted for clarity and are of standard configuration, readily adaptable by a person of ordinary skill in the art to the embodiments set forth herein, and are thus not further detailed here. As seen in FIG. 4(a), arterial needle 14 is configured to slide inside the lumen of the arterial sheath 15, and conversely arterial sheath 15 can slide over arterial needle 14. Guide wire 16 is configured to fit inside the lumen of arterial needle 14 so as to move along arterial needle 14. FIG. 4(b) shows a schematic top view of the arrangement of scalpel 17a, Doppler gel and antiseptic application needle 12a, and local anesthetic needle 13a relative to arterial needle 14, all of which are contained within upper unit 18 (partially shown in phantom for clarity). The arrows in FIG. 4(b) indicate movement directions of the foregoing components. As seen in FIG. 4(b), the axes and the directions of movement of scalpel 17a, arterial needle 14, Doppler gel and antiseptic application needle 12a, and local anesthetic needle 13a may form an angle with respect to each other so as to ensure that each of these surgical tools penetrate into a patient's skin at the proper and intended location, and likewise reach the desired location within the body of the patient with respect to the artery that is to receive arterial sheath 15.

Figure 5:
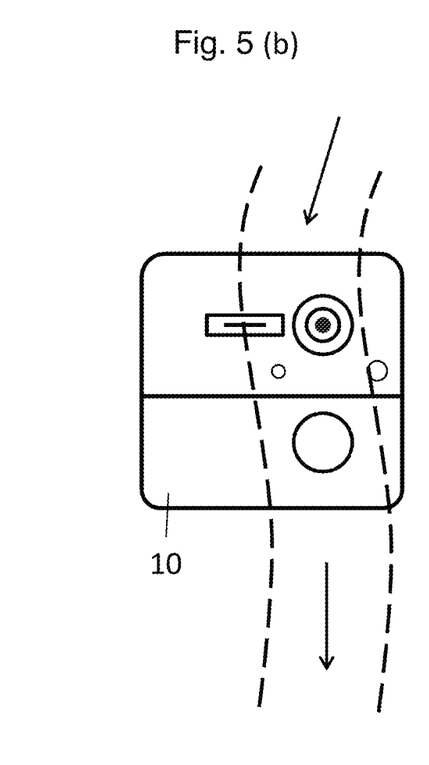
FIG. 5(a) shows a schematic diagram depicting a side view of the position of the arterial sheath placement device of FIG. 3(a), while in use, with respect to the groin and the femoral artery according to certain aspects of an exemplary embodiment of the invention.
FIG. 5(b) shows a schematic diagram depicting a front view of the position of the arterial sheath placement device of FIG. 3(a), while in use, with respect to the femoral artery according to certain aspects of an exemplary embodiment of the invention.

FIG. 5(a) shows a schematic diagram depicting a side view of the eFASP, while in use, with respect to a patient's thigh and the femoral artery according to an exemplary embodiment of the invention. As seen in FIG. 5(a), the head 10 of the device is disposed against (in contact with) the skin of the patient. FIG. 5(b) shows a schematic diagram depicting a front view of the position of the arterial sheath placement head 10 of the eFASP with respect to the femoral artery during use (as described in detail below) according to an exemplary embodiment of the invention.

Figure 6A:
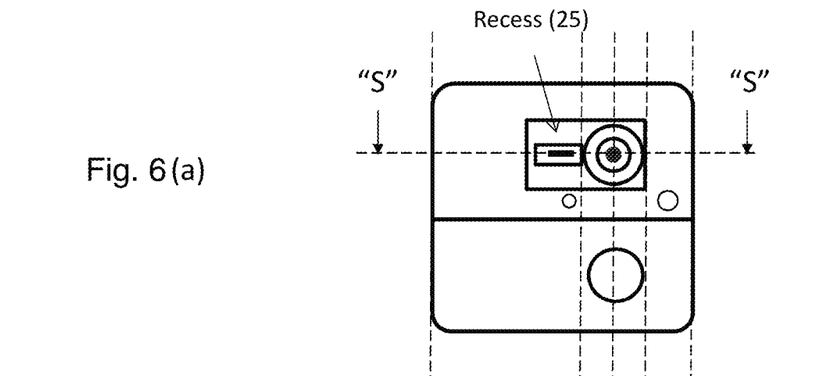
FIG. 6(a) shows schematically a front view of the head of an arterial sheath placement device according to further aspects of an exemplary embodiment of the invention.
Figure 6B:
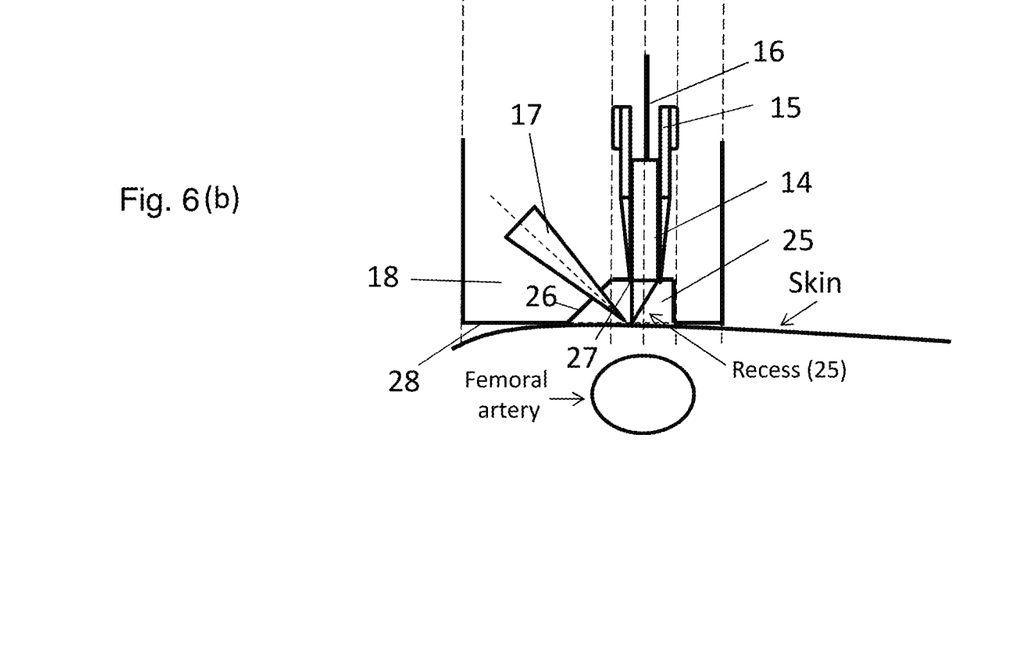
FIG. 6(b) shows schematically a cross-sectional view, through cross-section "S" in FIG. 6(a), of the arterial sheath placement head of an arterial sheath placement device according to further aspects of an exemplary embodiment of the invention.

FIGS. 6(a) and (b) show additional features in accordance with an exemplary embodiment of the invention. As shown in FIGS. 6(a) and 6(b), arterial sheath placement head 10 may include a recess 25 including an angled wall 26 extending between a sheath outlet wall 27 and skin contact wall 28, with scalpel port 17 positioned in angled wall 26 to point scalpel 17a towards the location at which arterial sheath 15 is configured to enter the skin. FIG. 6(a) shows a front view of arterial sheath placement head 10, and FIG. 6(b) schematically shows a cross-sectional view, through cross-section "S-S" in FIG. 6(a), of arterial sheath placement head 10. FIG. 6(b) shows the positions of arterial needle 14, arterial sheath 15, guide wire 16, and scalpel 17a with respect to each other and with respect to the patient's skin and femoral artery.

As mentioned above, the eFASP may include a plurality of mechanisms and electronic circuits configured to drive/operate the components within arterial sheath placement head 10. The mechanisms and electronic circuits may be incorporated in the arterial sheath placement head 10 and handle body 30. For example, the eFASP may include: a mechanism for driving Doppler gel and antiseptic application needle 12a and for injecting the Doppler gel and the antiseptic therefrom; a mechanism for driving local anesthetic needle 13a and for injecting anesthetic therefrom; a mechanism for driving arterial needle 14; a mechanism for driving arterial sheath 15; a mechanism for driving guide wire 16 (e.g., capstan wire drive 6 shown in FIG. 4(a)); and a mechanism for driving/operating scalpel 17a. The eFASP may further include mechanisms and/or electronic circuits for converting the operator's actions on trigger 40 (e.g., operator pushes trigger 40) to operations of the components in arterial sheath placement head 10 (e.g., pushing trigger 40 may cause local anesthetic needle 13a to exit from upper body 18 and advance so as to penetrate the skin of the patient; pushing the trigger may sequentially activate each step of the method for automatically placing arterial sheath 15). Such basic mechanical and electronic circuit devices for translating trigger 40 movement to movement of the other system components are routine, common elements easily adaptable to the embodiments set forth herein by a person of ordinary skill in the art, and are thus not further detailed here.

Further, the eFASP may include a plurality of electronic devices, microprocessors and memories. The electronic devices may be configured to receive signals from Doppler sensor 11 and the pressure transducers 20 and 21. The microprocessors and memories are configured to process signals and data received from the electronic devices, and to display on the LCD screen 50 (or any other device for visually displaying, or audibly signaling the operator) information about the status of the eFASP. Once again, such electronic devices, microprocessors and memories are quite common and easily adaptable to the embodiments set forth herein by a person of ordinary skill in the art, and are thus not further detailed here.

The method of operating the eFASP device (such as to perform the automatic placement of arterial sheath 15) and the functioning of the eFASP is explained hereinafter according to an exemplary embodiment of the invention and with reference to FIG. 7. In a stand-by mode (before beginning the medical procedure of placing arterial sheath 15), Doppler gel and antiseptic application needle 12a, anesthetic needle 13a, arterial needle 14, arterial sheath 15, guide wire 16, and scalpel 17a are all positioned inside their corresponding ports of arterial sheath placement head 10. Trigger 40 (similar to the trigger of a hand-held power drill) may be used to sequentially activate each step of the methods/procedures described hereinafter. LCD display screen 50 may indicate the status of the device and the steps/functions of the medical procedure.

Figure 7:
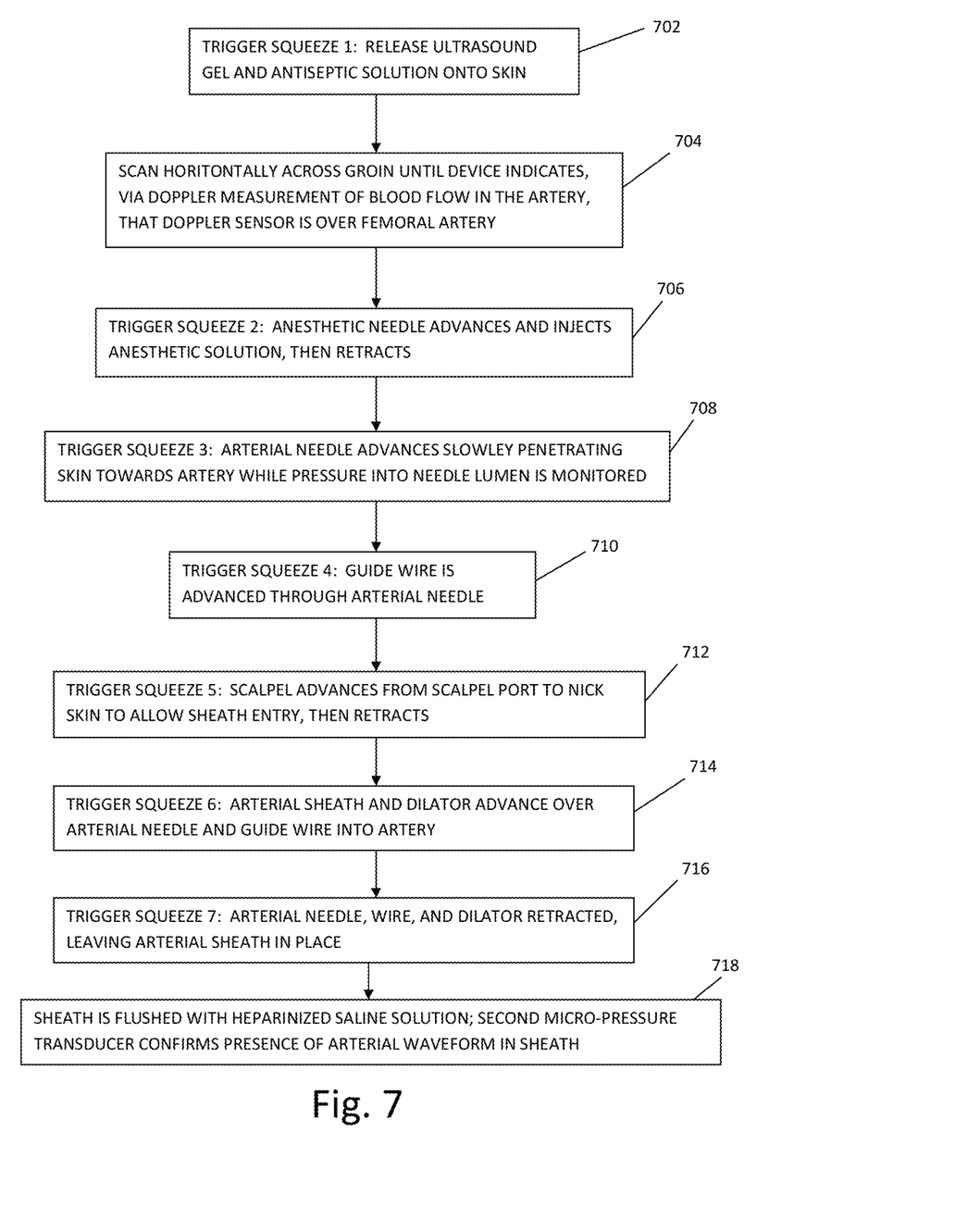
FIG. 7 is a flow chart depicting the steps of a method for using an arterial sheath placement device according to certain aspects of an exemplary embodiment of the invention.

As shown in FIG. 7, at step 702, an operator holds the eFASP device over the patient's femoral region and squeezes trigger 40 to release, via the tip of Doppler gel and antiseptic application needle 12a, a mixture of ultrasound gel and antiseptic solution onto the patient's skin. At step 704, the operator scans horizontally across the groin until the device indicates that its tip (i.e., the arterial sheath placement head 10, or more specifically Doppler sensor 11) is positioned over the artery that is to receive arterial sheath 15 (such as the patient's femoral artery), as indicated by an arterial Doppler signal detected by Doppler probe 11 (see FIGS. 3(b) and 4(a)). This may be indicated on display screen 50 by, for example, a blinking light, or by an audible alarm, or such other indicator as will be apparent to those skilled in the art. At step 706, the operator squeezes trigger 40 again, and local anesthetic needle 13a advances and injects anesthetic solution, and then retracts. The actions may be controlled by, for example, stepper motors within lower body control unit 19, the stepper motors being connected by splined shafts to disposable upper body 18. At step 708, the operator squeezes trigger 40 again and arterial needle 14 advances slowly from the disposable upper body 18 directly above the Doppler probe 11. Arterial sheath placement head 10 is positioned over the femoral region to ensure that when the Doppler sensor indicates that the device tip is over the femoral artery, arterial needle 14 is positioned to be inserted into the femoral artery. The operator will be trained to keep the device aligned generally with the patient's body so that the Doppler sensor and the arterial entry needle are both properly aligned over the femoral artery. Arterial needle 14 may be provided a micro-pressure transducer (e.g., GE NPC-100) that is monitored by lower body control unit 19. When lower body control unit 19 displays arterial waveforms in the needle lumen, at step 710 the operator squeezes trigger 40 again, and guide wire 16 in the disposable upper body 18 is advanced through the needle by dual capstan drive system 6 (as shown in FIG. 4(*a*)). When guide wire 16 has advanced approximately 15 cm, the operator is notified by display screen 50 to squeeze trigger 40 again, and at step 712 (upon such trigger squeeze) scalpel 17*a* (e.g., #11 scalpel blade) advances from scalpel port 17 to nick the patient's skin to allow sheath entry, and then retracts. At step 714, the next trigger squeeze causes arterial sheath 15 (and a dilator at a distal tip of arterial sheath 15) to advance over arterial needle 14 and guide wire 16 into the patient's artery. At step 716, the next squeeze of trigger 40 causes arterial needle 14, guide wire 16, and the dilator to retract, leaving the arterial sheath 15 in place. Finally, at step 718, arterial sheath 15 is then automatically flushed with heparinized saline solution and a second micro pressure transducer 21 (see FIG. 4(*a*)) confirms the presence of an arterial waveform in the sheath to the operator via display screen 50. The device improves upon the Seldinger technique (as shown in FIG. 2) by providing all required devices in a single, self-contained unit, and by making the process of arterial cannulation semi-autonomous.

The separation of lower body control unit 19 from disposable upper body 18 keeps the "per use" cost of the device low. Complex and expensive components (Doppler transducer, driver motors, control circuitry, display panels) are situated in the reusable lower body control unit 19. The self-contained nature of the device (incorporating Doppler, gel, anesthesia, scalpel, etc. in a single unit) and the ability to power the device with rechargeable batteries makes it potentially appealing for placement in ambulances, emergency rooms and other pre-hospital settings, and allows non-physicians to perform this procedure safely. This device has obvious appeal for military use in battlefield, transport and pre-hospital settings.

While the exemplary embodiments have been shown and described, it will be understood by those skilled in the art that various changes in form and details may be made thereto without departing from the spirit and scope of the present disclosure as defined by the appended claims.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. An automated emergency arterial sheath placement device, comprising:
    a body including a handle;
    an arterial sheath placement head attached to said body, said arterial sheath placement head comprising a non-invasive artery locator and an arterial sheath insertion device;
    a manually operable actuator;
    an arterial needle and a first pressure transducer detachably connected to said arterial needle; and
    an arterial sheath and a second pressure transducer mounted on said arterial sheath and configured to measure pressure inside a lumen of the arterial sheath;
    wherein said arterial sheath insertion device is positioned with respect to said artery locator so as to position said arterial sheath insertion device over an artery that has been located by said artery locator, and wherein said automated emergency arterial sheath placement device is configured to cause said arterial sheath insertion device to install said arterial sheath in a patient's artery upon sequential activation of said actuator.

2. The automated emergency arterial sheath placement device of claim 1, wherein said arterial needle, said arterial sheath, and a guide wire are arranged concentrically in said arterial sheath insertion device.

3. The automated emergency arterial sheath placement device of claim 2, said arterial sheath placement head further comprising an upper body detachably connected to a lower body, wherein said arterial sheath insertion device is positioned within said upper body, and wherein said artery locator is positioned within said lower body.

4. The automated emergency arterial sheath placement device of claim 1, said arterial sheath placement head further comprising:
    a scalpel;
    a Doppler gel application needle; and
    an anesthetic needle;
    wherein a longitudinal axis of each of said scalpel, said Doppler gel application needle, and said anesthetic needle is situated at an angle with respect to a longitudinal axis of said arterial needle.

5. The automated emergency arterial sheath placement device of claim 4, wherein said automated emergency arterial sheath placement device is further configured to cause said scalpel, said Doppler gel application needle, and said anesthetic needle to sequentially engage a patient's body at a location over said located artery upon sequential activation of said actuator.

6. The automated emergency arterial sheath placement device of claim 1, further comprising a display configured to indicate placement of said arterial sheath insertion device over said artery in response to detection of said artery by said artery locator.

7. A method for performing automated emergency arterial sheath placement, comprising the steps of:
    providing an automated emergency arterial sheath placement device, comprising:
        a body including a handle;
        an arterial sheath placement head attached to said body, said arterial sheath placement head comprising a non-invasive artery locator and an arterial sheath insertion device;
        a manually operable actuator;
        an arterial needle and a first pressure transducer detachably connected to said arterial needle; and
        an arterial sheath and a second pressure transducer mounted on said arterial sheath and configured to measure pressure inside a lumen of the arterial sheath;
        wherein said arterial sheath insertion device is positioned with respect to said artery locator so as to position said arterial sheath insertion device over an artery that has been located by said artery locator, and wherein said automated emergency arterial sheath placement device is configured to cause said arterial sheath insertion device to install said arterial sheath in a patient's artery upon sequential activation of said actuator;
    positioning said automated emergency arterial sheath placement device over a patient's femoral region;

moving said automated emergency arterial sheath placement device across the patient's groin until said artery locator detects that said arterial sheath insertion device is positioned over a femoral artery of the patient; and sequentially engaging said actuator to cause said arterial sheath insertion device to insert said arterial sheath into the femoral artery of the patient.

8. The method of claim 7, wherein said arterial sheath placement device further comprises a guide wire, and wherein said step of sequentially engaging said actuator further comprises the step of engaging said actuator to cause said arterial needle and said guide wire to retract into said arterial sheath placement head while leaving said arterial sheath positioned within the patient's femoral artery.

9. The method of claim 7, further comprising the step of monitoring arterial pressure waveforms in said arterial needle with said first pressure transducer.

10. The method of claim 7, said arterial sheath placement head further comprising a Doppler gel application needle, wherein the step of sequentially engaging said actuator further comprises the step of engaging said actuator to cause said Doppler gel application needle to release a mixture of ultrasound gel and antiseptic solution onto the patient's skin.

11. The method of claim 7, said arterial sheath placement head further comprising an anesthetic needle, wherein said step of sequentially engaging said actuator further comprises the step of engaging said actuator to cause said anesthetic needle to advance from said arterial sheath placement head, to inject anesthetic solution, and to retract into said arterial sheath placement head.

12. The method of claim 7, said arterial sheath placement head further comprising a scalpel, wherein the step of sequentially engaging said actuator further comprises the step of engaging said actuator to cause said scalpel to advance from said arterial sheath placement head and to nick the patient's skin to allow entry of said arterial sheath.

* * * * *